(12) United States Patent
Blumberg et al.

(10) Patent No.: US 7,012,687 B2
(45) Date of Patent: Mar. 14, 2006

(54) SPECTRAL ANALYSIS WITH EVANESCENT FIELD EXCITATION

(75) Inventors: Girsh Blumberg, New Providence, NJ (US); Brian S Dennis, Chatham, NJ (US)

(73) Assignee: Lucent Technologies Inc., Murray Hill, NJ (US)

( * ) Notice: Subject to any disclaimer, the term of this patent is extended or adjusted under 35 U.S.C. 154(b) by 63 days.

(21) Appl. No.: 10/838,594

(22) Filed: May 4, 2004

(65) Prior Publication Data

US 2005/0249478 A1    Nov. 10, 2005

(51) Int. Cl.
*G01J 3/44*    (2006.01)
*G02B 6/00*    (2006.01)

(52) U.S. Cl. ............... 356/301; 356/317; 356/318; 356/445; 385/12; 385/43; 385/123; 385/128

(58) Field of Classification Search ............... 356/301, 356/317, 318, 445
See application file for complete search history.

(56) References Cited

U.S. PATENT DOCUMENTS

| | | | |
|---|---|---|---|
| 4,781,458 A | 11/1988 | Angel et al. ............... 356/301 |
| 5,627,922 A * | 5/1997 | Kopelman et al. ............ 385/12 |
| 5,708,735 A * | 1/1998 | Benson et al. ............... 385/12 |
| 5,789,742 A | 8/1998 | Wolff ...................... 250/227.11 |
| 5,789,743 A | 8/1998 | Van Rosmalen ............ 250/234 |
| 5,864,397 A * | 1/1999 | Vo-Dinh .................... 356/301 |
| 5,866,430 A | 2/1999 | Grow ......................... 436/172 |
| 5,973,316 A | 10/1999 | Ebbesen et al. ............ 250/216 |
| 5,994,691 A | 11/1999 | Konada ..................... 250/234 |
| 6,038,363 A * | 3/2000 | Slater et al. ................. 385/147 |
| 6,040,191 A | 3/2000 | Grow ......................... 436/172 |
| 6,040,936 A | 3/2000 | Kim et al. ................... 359/245 |
| 6,052,238 A | 4/2000 | Ebbesen et al. ............ 359/738 |
| 6,063,898 A | 5/2000 | Endo et al. ................. 528/411 |
| 6,236,033 B1 | 5/2001 | Ebbesen et al. ............ 250/216 |
| 6,285,020 B1 | 9/2001 | Kim et al. ................... 250/216 |
| 6,558,958 B1 | 5/2003 | Pilevar et al. .............. 436/518 |
| 6,610,351 B1 | 8/2003 | Shchegolikhin et al. ....... 427/7 |
| 2002/0056816 A1 | 5/2002 | Stark ........................ 250/493.1 |
| 2002/0076729 A1 | 6/2002 | Tobias et al. ............... 435/712 |
| 2003/0036204 A1 | 2/2003 | Stark et al. ................. 436/172 |

FOREIGN PATENT DOCUMENTS

| | | |
|---|---|---|
| DE | 102 17 948 | 11/2003 |
| WO | WO 01/52329 A1 | 7/2001 |
| WO | WO 02/095070 A2 | 11/2002 |
| WO | WO 03/019245 A2 | 3/2003 |

OTHER PUBLICATIONS

U.S. Appl. No. 10/824,245, filed Apr. 14, 2004, Blumberg.
U.S. Appl. No. 10/350,780, filed Jan. 24, 2003, Blumberg et al.
"Learn NSOM" published online at www.Nanonics.co.il by Nanonics Imaging Ltd. Prior to Apr. 12, 2004 (4 pages).

(Continued)

*Primary Examiner*—Frank G. Font
*Assistant Examiner*—Michael P. Mooney
(74) *Attorney, Agent, or Firm*—John F. McCabe (57) ABSTRACT

An apparatus includes an optical fiber and a light collection device. The optical fiber has an untapered segment and a down-tapered segment. The light collection device has an optical aperture that collects light emitted by a sample in response to the sample being located outside and adjacent a lateral surface of the down-tapered segment. The optical aperture blocks light emitted from ends of the optical fiber.

20 Claims, 5 Drawing Sheets

OTHER PUBLICATIONS

"NSOM System Comparisons" published online at www.Nanonics.co.il by Nanonics Imaging Ltd. Prior to Apr. 12, 2004 (11 pages).

U.S. Appl. No. 10/824,245, filed May 5, 2004, Blumberg.

Tuan Vo-Dinh, "Nanobiosensors: Probing the Sanctuary of Individual Living Cells," *Journal of Cellular Biochemistry Supplement*, No. 39, (2002), pp. 154-161.

Volker Deckert, et al, "Near-Field Surface-Enhanced Raman Imaging of Dye-Labeled DNA with 100-nm Resolution," *Analytical Chemistry*, vol. 70, No. 13, (Jul. 1, 1998), pp. 2646-2650.

European Search Report, Appt. 05252546.6-2204 PCT/, (Oct. 24, 2005).

* cited by examiner

SPECTRAL ANALYSIS WITH EVANESCENT FIELD EXCITATION

BACKGROUND

1. Field of the Invention

This invention relates generally to spectrographic measuring methods and systems.

2. Discussion of the Related Art

Spectrally analyzing a sample typically involves illuminating the sample with light and measuring the intensity of absorbed, scattered, or fluoresced light by the illuminated sample as a function of wavelength. The sensitivity of a spectral analysis may depend strongly on several lighting conditions.

One important lighting condition relates to the intensity of background light in the light detector used for the spectral analysis. Background light may include illumination light and light scattered, absorbed, or fluoresced outside of the sample.

Background light may wash out absorption, scattering, and/or fluorescence by the sample.

Another important lighting condition relates to the intensity of illumination light at the sample. Typically, the spectral response of a sample will be larger if the intensity of illumination light therein is larger. The intensity of illumination light in a sample is limited by physical constraints. For example, diffraction limits the ability to focus a light beam to a diameter smaller than the wavelength. Thus, diffraction will limit the ability to increase illumination intensities in a sample through focusing.

During spectral analysis, it is often desirable to produce lighting conditions that increase overall sensitivities.

SUMMARY

Various embodiments can perform spectral analysis under conditions that reduce the intensity of background light in light collection devices while providing high excitation field intensities in the sample. In particular, a sample is subjected to evanescent fields produced by light propagating in an optical fiber and spectral measurements are obtained from light emitted, radiated, or scattered outside the optical fiber by the sample. The optical fiber substantially confines illumination light so that the spectral response of the sample is not washed out by background illumination light.

One embodiment features an apparatus having an optical fiber and a light collection device. The optical fiber has an untapered segment and a down-tapered segment. The light collection device has an optical aperture that collects light emitted by a sample in response to the sample being located outside and adjacent a lateral surface of the down-tapered segment. The optical aperture blocks light emitted from ends of the optical fiber.

Some of the apparatus include a light intensity detector that measures light intensities collected by the light collection device and determines a secondary emission spectrum of the sample from measured light intensities.

Another embodiment features a method for spectrally analyzing a sample. The method includes transmitting light into a clad optical fiber. The light propagates into a down-tapered or partially unclad segment of the optical fiber and produces evanescent fields at a sample. The sample is located both laterally adjacent and outside the down-tapered or partially unclad segment. The method includes collecting light that the sample emits into an optical aperture in response to the transmitting of light. The optical aperture opens toward a lateral surface of the down-tapered or partially unclad segment. The method includes measuring intensities of the collected light.

Some embodiments of the method also include determining a secondary emission, luminescence or Raman emission spectrum of said sample from said measured intensities.

In some embodiments of the above apparatus and method, an untapered segment of the optical fiber functions as a single-mode optical fiber.

Another embodiment features an apparatus that includes a single-mode optical fiber and a light collection device. The single-mode optical fiber has an optical core and an optical cladding and has an untapered segment and a tip segment. In the tip segment, a portion of the cladding is removed thereby exposing a lateral surface of the optical core. The light collection device has an optical aperture that collects light emitted by a sample. The sample is located laterally adjacent to the exposed lateral surface in the tip segment. The optical aperture blocks light emitted that is from the ends of the optical fiber.

BRIEF DESCRIPTION OF THE DRAWINGS

Herein, similar reference numerals indicate features with similar functions.

Herein, dimensions of some features are magnified or reduced to better illustrate the embodiments.

The illustrative embodiments are described more fully with reference to the accompanying figures and detailed description. The inventions may, however, be embodied in various forms and are not limited to embodiments described herein.

DETAILED DESCRIPTION OF ILLUSTRATIVE EMBODIMENTS

In various types of spectral analysis, background light may act as noise that washes out the desired light. For example, in Raman spectral analysis, background light intensities can be orders of magnitude larger than the intensity of the Raman light that one wants to measure. The Raman light often has an intensity that is much weaker than the intensity of the illumination light used to excited molecules of the sample. For that reason, Raman spectra are often difficult to measure near the wavelength of the illumination light, i.e., stray light. Eliminating stray illumination light may significantly increase sensitivities of spectral analysis based on Raman light.

Various embodiments significantly reduce stray light intensities at and near the wavelength used to illuminate a sample.

Figure 1:
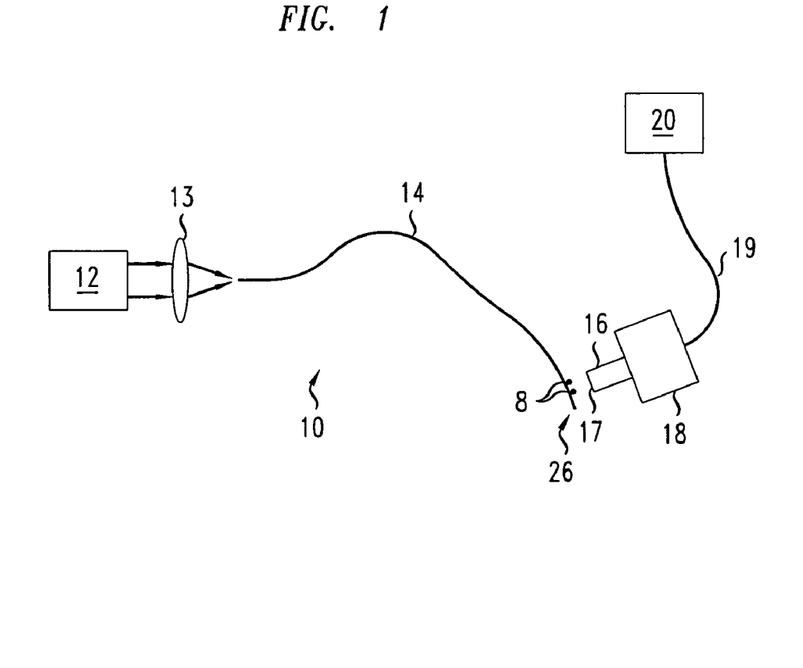
FIG. 1 is a block diagram of a system for performing spectral analysis of a sample.
Figure 2:
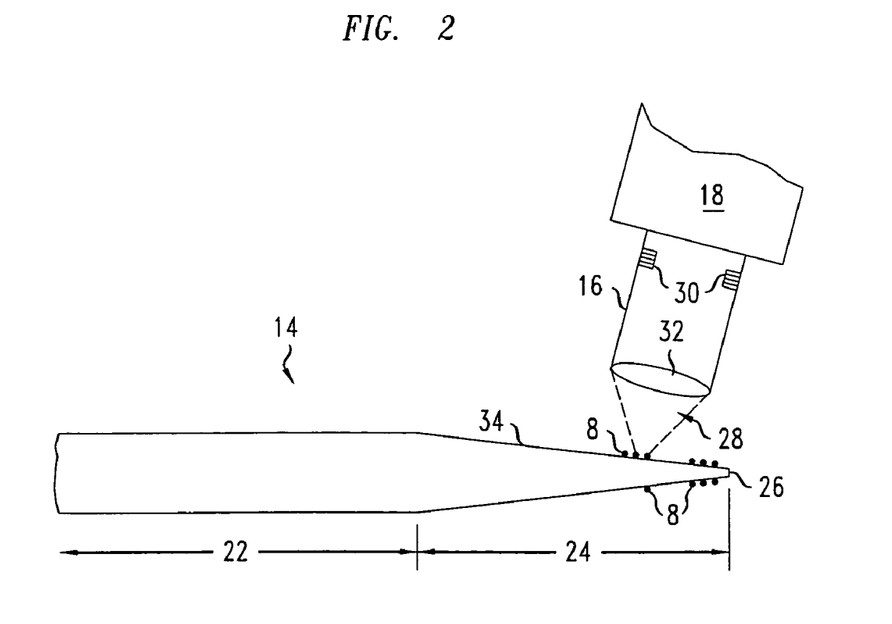
FIG. 2 is an enlarged cross-sectional view of a tip portion of the illumination optical fiber used in one embodiment of the system of FIG. 1.

FIGS. 1 and 2 illustrate a system 10 for spectrally analyzing a sample formed by chemical species 8. The system 10 includes an illumination source 12, an optical fiber 14, a light collection system 16, an optical spectrometer 18, and a data processor 20.

The illumination source 12 produces light that may be high intensity and may be monochromatic and transmits the illumination light to an end of optical fiber 14 via focusing optics 13. Exemplary illumination sources include various types of lasers, e.g., semiconductor diode lasers.

The optical fiber 14 includes an untapered segment 22 and a tapered segment 24. The untapered segment 22 functions as a standard single-mode optical fiber at the wavelength produced by illumination source 12. The tapered segment 24 gradually down-tapers the diameter of the untapered segment 22 to a smaller diameter of end face 26. Herein, the outer diameter of an optical cladding layer and/or optical core becomes smaller in a down-tapered optical fiber segment. While the end face 26 may have a diameter significantly smaller than the diameter of the untapered segment 22, the down-tapered segment 24 does not laterally leak light at the wavelength of the illumination source 12. Exemplary down-tapered segments 24 are made by pulling a standard single-mode optical fibers according to techniques known in the art.

The light collection device 16 has an entrance aperture 17 that opens towards lateral surface 34 of down-tapered segment 24. The entrance aperture 17 collects light that is emitted from a local lateral region 28 laterally adjacent the lateral surface 34. The sample includes a chemical species 8 located on the lateral region 28.

Light collection device 16 includes an optical magnifier 32, a field aperture 30, and an optical spectrometer 18. The optical magnifier 32 is a single lens or multi-lens magnification system. The field aperture 30 is located between the optical magnifier 32 and the optical spectrometer 18. The field aperture stops substantially all background light except light that passes through local lateral region 28. The optical spectrometer 18 is a diffraction-based spectrometer that includes a light intensity detector. In some applications, Raman multistage spectrometers may be advantageous, because such spectrometers control internally generated stray light. Exemplary optical spectrometers may include the model T64000 triple Raman spectrometer, the model U1000 double spectrometer, and the model LabRam HR 800 high resolution Raman analyzer, which are manufactured by Jobin Yvon Inc. of 3880 Park Avenue, Edison, N.J. 08820-3012 USA (www.jobinyvon.com).

Optical magnifier 32 is located so that lateral region 28 is approximately on the magnifier's focal point. Preferably, the optical magnifier 32 projects a diffraction limited spot, e.g., having a radius of about ½ the illumination wavelength, onto the field stop 30 of a spectrometer 19. Then, only light from the cone defined by region 28 will pass through slit-shaped or circular-shaped field aperture 30 of light collecting device 16. Since illumination light does not leak from down-tapered segment 24 via region 28, illumination light will not wash out weak light emissions by the sample's chemical species 8 into the light collection device 16.

Exemplary optical magnifiers 32 include microscope objective lenses with high magnifications, e.g., about 10 to 100. Due in part to the high magnification, the light collection device 16 has a field of view that is limited to a small lateral region 28. The light collection device 16 has a field of view does not include either end of optical fiber 14. The ends of optical fiber are blocked out of the field of view, e.g., by field stop 30. Typically, the field of view is further limited to a solid angle that down-tapered segment 24 subtends at the light collection device 16. The restricted field of view reduces collection of stray light in the light collection device 16 and optical spectrometer 18. Such stray light might otherwise wash out light from the sample that is being analyzed.

The light collection device 16 may also collect all light that is emitted into a large solid angle about the sample due to the short focal length and close positioning of the optical magnifier to region 28. For example, the light collection device 16 may collect all light emitted by the sample into a solid angle of π or more.

Optical spectrometer 18 measures intensities of collected light in a selected wavelength range. The selected range may correspond to wavelengths of Raman light or secondary emission light that chemical species 8 produces when subjected to the wavelength of source 12. For example, the measured light may be produced when the chemical species 8 is illuminated by free propagating light or is exposed to evanescent fields of light in the wavelength range that untapered portion 22 of optical fiber 14 is adapted to transport.

Data processor 20 receives electrical data for measured light intensities from optical spectrometer 18 via cable 19. From the data, the data processor 20 produces a secondary emission spectrum for the chemical species 8, e.g., a Raman spectrum.

In lateral region 28, chemical species 8 is subjected to evanescent fields that are produced by light propagating in optical fiber 14. The evanescent fields excite the chemical species 8 to secondarily emit light. The optical fiber 14 is configured to not leak illumination light through the region 28 even though the fiber's diameter at the region 28 may be significantly less than the fiber's diameter along untapered segment 22. The lack of such light leakage may, in part, be due to the untapered segment 22, which functions as a single-mode optical fiber at the wavelength of source 12. In the untapered segment 22, the propagation mode has a high intensity at the center of the optical fiber. For that reason, the mode will couple only weakly to cladding modes in down-tapered segment 24, i.e., couples only weakly to modes that could leak from the down-tapered segment 24. The diameter of down-tapered segment 24 is large enough to avoid such leakage, and small enough so that the evanescent fields of the propagating mode extend past the outer surface 34 in the lateral region 28.

For these reasons, the down-tapered segment 24 produces intense evanescent fields adjacent its lateral surface 34 without causing light leakage therefrom. In region 28, the sample's chemical species 8 is subjected to "evanescent fields" rather than to free propagating illumination light. Thus, illumination light will be substantially absent in the collected light and will not wash out ultra-weak light emissions by the chemical species 8 located in the region 28 even if the ultra-weak emissions are at a wavelength close to that of the illumination light.

Similarly, impurities of optical fiber 14 will not generate substantial noise light in light collection device 16. While such impurities may emit Raman light in response to the illumination light propagating in down-tapered segment 24, much of such emissions by impurities will be confined to propagate in the down-tapered segment 24 rather than being emitted through region 28 as free propagating light.

Due to the significant elimination of stray light at and near the illumination wavelength, system 10 is advantageous for measuring weak secondary emission spectra of chemical species 8, e.g., weak Raman spectra.

Exemplary embodiments of down-tapered segment 24 have a fine diameter adjacent lateral region 28. There, the diameter of the down-tapered segment 24 may be smaller than the wavelength of the illumination light so that very strong evanescent fields are generated in the lateral region 28. For such small diameters, the evanescent fields can be very strong in the space lateral and adjacent to the down-tapered segment 24. At the region 28, exemplary down-tapered segments 24 have diameters that could be much smaller than the illumination wavelength. Exemplary optical fibers 14 having down-tapered segments 24 formed by pulling standard single-mode optical fibers. Optical fibers with such down-tapered tip segments are commercially available as a bare NSOM optical fiber probes from Nanonics Imaging Ltd. at Manhat Technology Park, Malcha, Jerusalem 91487. Israel (www.nanonics.co.il).

FIGS. 3A–3E illustrate optical fiber devices 14A–14E that replace optical fiber device 14 in other embodiments of system 10 of FIG. 1.

Referring to FIGS. 3A–3E, optical fiber devices 14A–14D include single-mode optical fiber 14, wherein metal layers 36A, 36B, 36C, 36D cover outer surface 34 of the down-tapered segment 24 of the optical fiber 14. Exemplary metal layers 36A–36D are films of gold, platinum and/or silver with a thickness about equal to the surface plasmon penetration depth or thinner.

Each optical fiber device 14A–14D generates surface plasmons along down-tapered segment 24 in response to illumination being received in untapered segment 22 from the opposite end of optical fiber 14. The surface plasmons propagate along the lateral surface 34 between metal layers 36A–36D and the optical fiber 14. The surface plasmons contribute to evanescent fields that excite the sample chemical species 8 located on external surface 38 of the metal layers 36A–36D. Their contributions to the evanescent field can enhance light emissions by the sample chemical species 8.

Figure 3A:
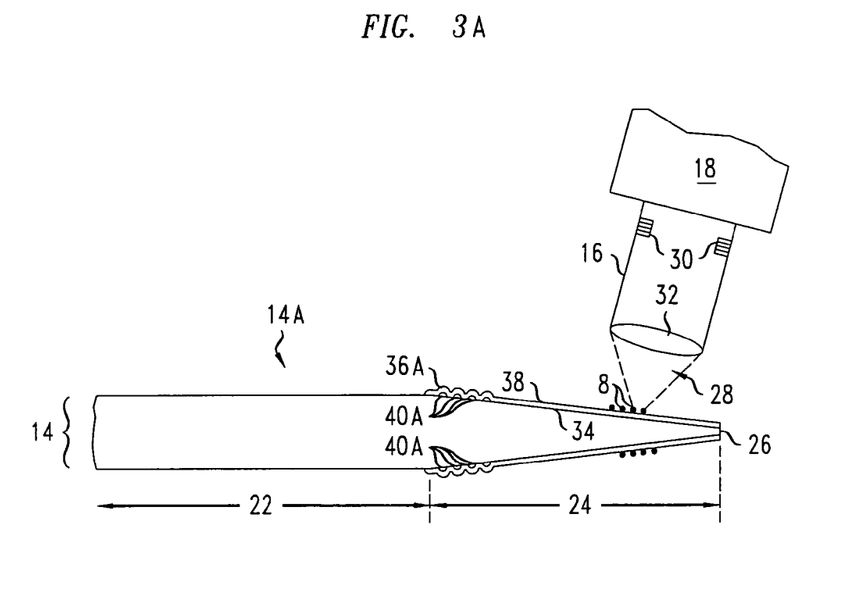
FIGS. 3A–3E are enlarged cross-sectional views of illumination optical fiber devices for other embodiments of the system of FIG. 1.
Figure 3B:
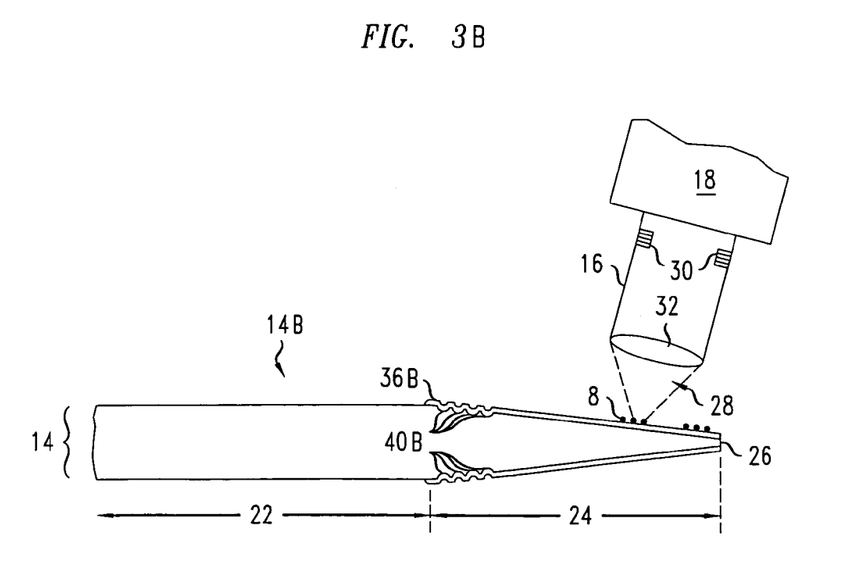
Figure 3C:
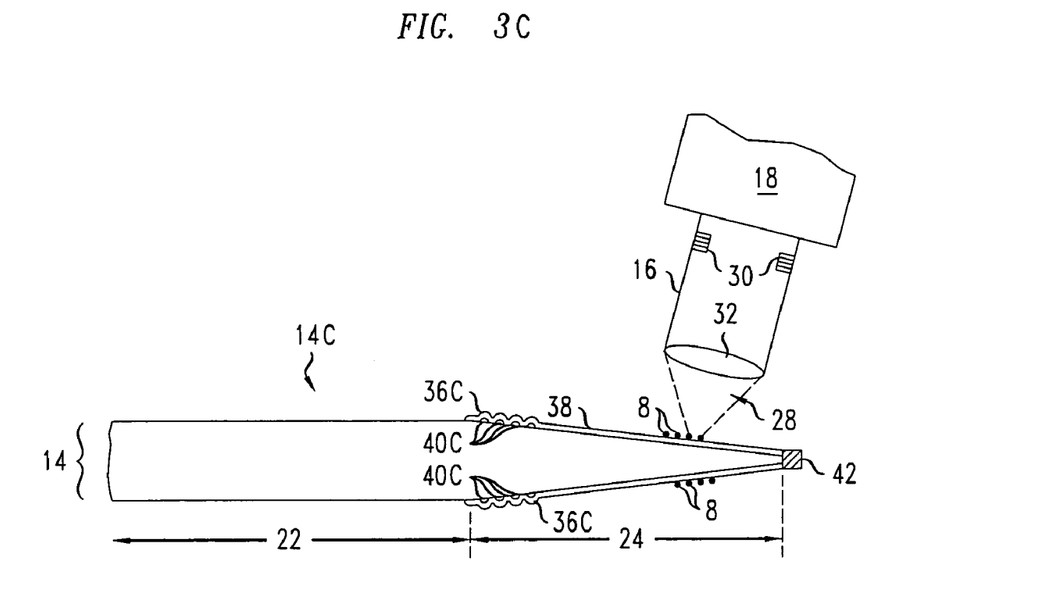

The optical fiber devices 14A–14C include one or more arrays of structures 40A, 40B, 40C. The arrays of structures 40A, 40B, 40C are located adjacent to untapered segment 22 to convert illumination light from untapered segment 22 into surface plasmons that propagate along down-tapered segment 24. In each array, the structures 40A–4C have similar cross-sectional profiles and are regularly distributed along the axis of a part of the down-tapered segment 24, i.e., to form gratings. Exemplary forms for the structures 4A–40C are rings that encircle all or a portion of the circumference of the down-tapered segment 24.

Referring to FIGS. 3A and 3B, structures 40A, 40C of optical fiber devices 14A, 14C are dielectric or semiconductor bumps or dimples that are located on outer lateral surface 34 of down-tapered segment 24. The bumps have dielectric constants that substantially differ from the dielectric constant of either the silica glass of optical fiber 14 or the metal of metal layer 36A. Exemplary bumps are fabricated of silicon nitride.

The optical fiber devices 14A, 14C may be fabricated from single-mode fibers with down-tapered tip segments, e.g., pulled-tip optical fibers as described above. One fabrication method includes lithographically forming a mask on the down-tapered tip segment 24 of the optical fiber 14, depositing dielectric on the masked down-tapered tip segment 24, and then performing a plasma etch to strip remaining mask material and complete fabrication of the regular arrays of structures 40A, 40C. The fabrication method also includes performing an evaporation-deposition of metal layer 36A, 36C over the down-tapered segment 24 and the structures 40A, 40C. Exemplary processes suitable for fabricating optical fiber devices 14A, 14C are, e.g., described in U.S. patent application Ser. No. 10/824,245 filed by Girsh Blumberg on Apr. 14, 2004 (Herein, the '245 patent application), which is incorporated herein by reference in its entirety.

In optical fiber device 14B, structures 40B are dimples of metal layer 36B that extend to fill ring-like pits in outer surface 34 of down-tapered segment 24.

The optical fiber devices 14B may also be fabricated from single-mode fibers having down-tapered tip segments, e.g., pulled-tip optical fibers as described above. The fabrication includes lithographically forming a mask on the down-tapered tip segment 24, etching the down-tapered tip segment 24 with a glass etchant, and then, plasma etching to strip remaining mask material. The etch steps produce a regular array of ring-shaped pits in outer lateral surface 34 of the down-tapered tip segment 24. The fabrication includes performing an evaporation-deposition of metal layer 36B over the down-tapered segment 24 to fill in the ring shaped pits and produce metal layer 36B and the array of structures 40B. Exemplary processes suitable for fabricating optical fiber devices 14B are, e.g., described in the '245 patent application.

Optical fiber devices 14C includes a metallic resonator that covers end face 26 of optical fiber 14. The metallic resonator reflects illumination light can produce standing wave field distributions in down-tapered segment 24. Such field distributions may be advantageous in producing evanescent fields for exciting sample chemical species 8, which are located on external surface 38 of metal layer 36C.

Figure 3D:
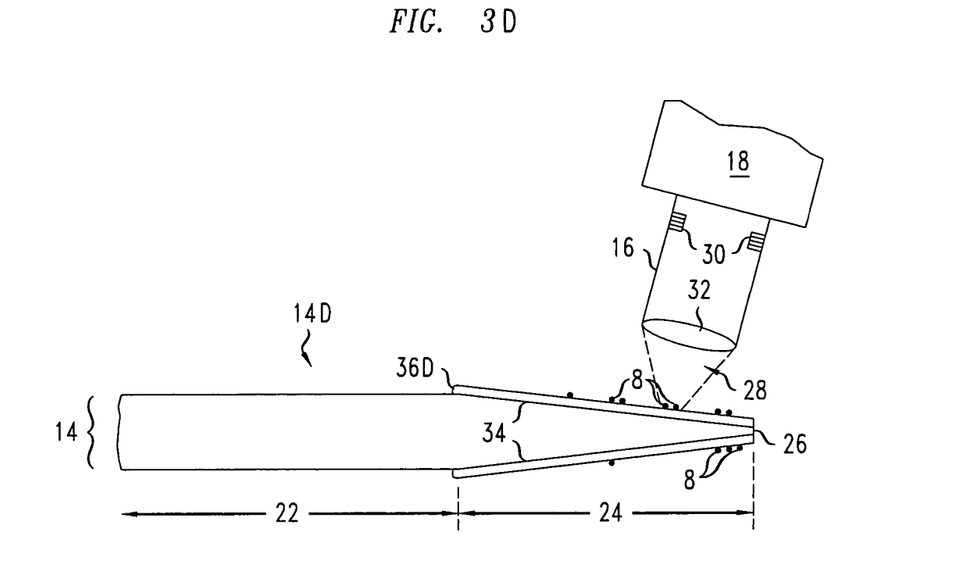

Referring to FIG. 3D, optical fiber device 14D has a down-tapered segment 24 whose diameter at region 28 is significantly smaller than the wavelength of the illumination light, which single-mode optical fiber 14 is adapted to transport. The smallness of the diameter of this portion of the down-tapered segment 24 should cause propagating light to produce surface plasmons along surface 34 without a periodic array of structures thereon.

Figure 3E:
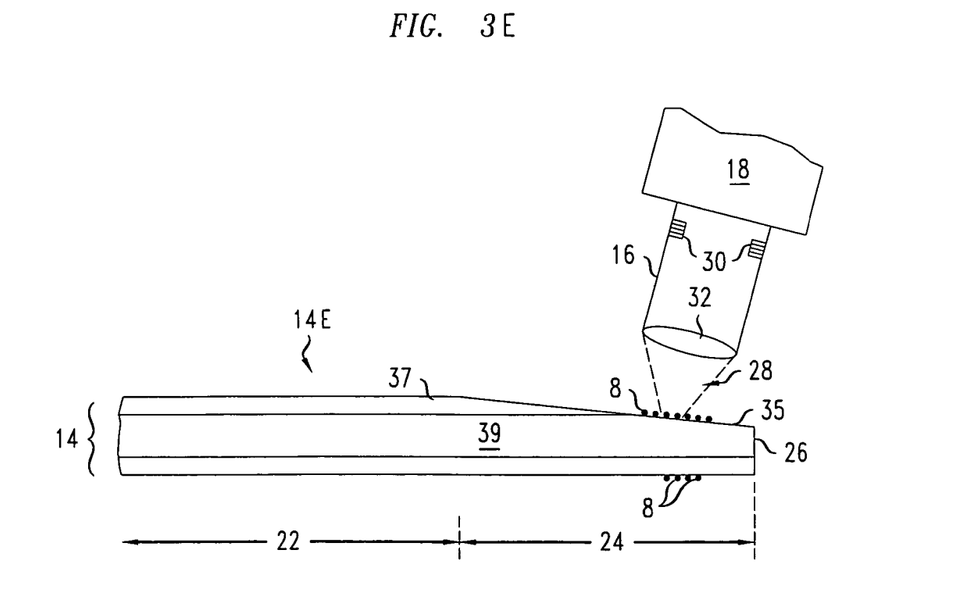

Referring to FIG. 3E, optical fiber device 14E has a tip segment 25 where optical cladding 37 has been partially (not shown) or completely removed, e.g., via a standard chemical mechanical polishing process. Due to the removal, lateral surface 35 of the optical core 39 of the single-mode optical fiber 14 is laterally exposed in region 28 of the tip segment 25. The lateral surface 35 has been fabricated to make a small angle with the central axis of the optical core 39. The inventors believe that such a structure should produce evanescent fields in lateral region 28 rather than freely radiating illumination light provided that the angle between the lateral surface 35 and the central axis of the optical core 39 is small enough. Furthermore, removing the typically thick cladding layer 37 substantially increases intensities of illumination fields in region 28 thereby increasing the excitation that such fields produce in the sample chemical species 8 located on the outer lateral surface 35.

Figure 4:
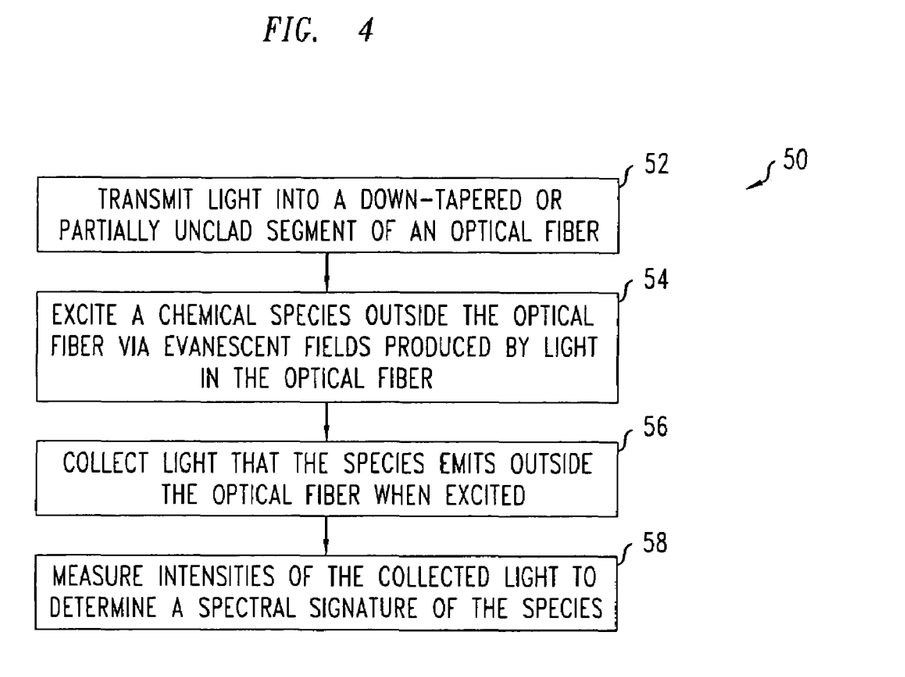
FIG. 4 is a flow chart illustrating a method of spectrally analyzing a sample with the system of FIG. 1.

FIG. 4 illustrates a method 50 of spectrally analyzing a chemical species with system 10 of FIG. 1 using, e.g., optical fiber 14 shown in FIG. 2 or one of optical fiber devices 14A–14E shown in FIGS. 3A–3E.

The method 50 includes transmitting illumination light into an optically clad single-mode optical fiber so that the light propagates into a down-tapered or partially unclad segment of the optical fiber (step 52). In the down-tapered or partially unclad segment, the illumination light does not leak out of the lateral surface of the optical fiber in part, because the light has been excited by the propagating mode of the single-mode segment of the optical fiber and the down-tapered segment has an appropriate diameter. Exemplary optical fibers 14 with suitably down-tapered segments or partially unclad segments include segments 24, 25 as shown in FIGS. 2, 3A, 3B, 3C, 3D, and 3E.

The method 50 includes exciting a sample chemical species with evanescent electromagnetic fields produced adjacent the down-tapered segment or partially unclad segment of the optical fiber in response to transmitting illumination light therein (step 54). The sample chemical species is located both outside and laterally adjacent to the down-tapered or partially unclad segment of the optical fiber. In some embodiments, the evanescent fields are produced by the illumination light in the down-tapered or partially unclad segment. In other embodiments, the illumination light produces surface plasmons that propagate along the lateral surface of the down-tapered or partially unclad segment, and the surface plasmons produce, at least, a portion of the evanescent fields.

The method 50 includes collecting light emitted by the sample chemical species in response to being excited (step 56). A light collection device has an entrance aperture that opens toward a lateral surface of the down-tapered or partially unclad segment. The light collection device may include one or more optical lenses and field apertures, e.g., as shown for device 16 of FIGS. 2, 3A–3E. The light collection device blocks light outside of a solid angle subtended by the down-tapered or partially unclad segment thereby reducing background light therein. In particular, the light collection device blocks illumination light from the ends of the optical fiber.

The method 50 includes measuring intensities of collected light and determining a spectrum of the sample chemical species from the measured intensities (step 58). Exemplary spectra include secondary emission and Raman spectra.

Other embodiments of the invention will be apparent to those skilled in the art in light of the specification, drawings, and claims of this application.

What is claimed is:

1. An apparatus, comprising:
    an optical fiber having an untapered segment and a down-tapered segment; and
    a light collection device having an optical aperture configured to collect light emitted by a sample in response to the sample being located outside the down-tapered segment and adjacent a lateral surface of the down-tapered segment; and
    wherein the optical aperture of the light collection device is configured to block light emitted from ends of the optical fiber.

2. The apparatus of claim 1, wherein the untapered segment of the optical fiber is configured to function as single-mode optical fiber.

3. The apparatus of claim 1, wherein the light collection device is configured to block light received from outside of a solid angle, the solid angle being subtended at the light collection device by the down-tapered segment.

4. The apparatus of claim 1, further comprising a spectrometer configured to measure light intensities collected by the light collection device and to determine a Raman or luminescence spectrum of a chemical species of the sample from the measured light intensities.

5. The apparatus of claim 2, wherein the down-tapered segment is configured to subject the sample to evanescent fields.

6. The apparatus of claim 2, wherein the optical aperture is configured to collect light emitted by the sample into a solid angle of at least R.

7. The apparatus of claim 2, further comprising:
    a metal layer having an inner surface located on a portion of the lateral surface of the down-tapered segment; and
    wherein the optical aperture is configured to collect light emitted by a chemical species located on an outer surface of the metal layer.

8. The apparatus of claim 7, further comprising
    a spectrometer configured to measure light intensities collected by the light collection device and to determine a Raman or luminescence spectrum of the chemical species from the measured light intensities.

9. The apparatus of claim 7, wherein one of a surface of the metal layer and the lateral surface of the down-tapered segment comprises an array of structures regularly distributed along a portion of a central optical axis of the optical fiber.

10. The apparatus of claim 7, wherein near the sample a diameter of the down-tapered portion is not larger than a wavelength of light that the single-mode fiber is configured to carry.

11. A method for spectrally analyzing a sample, comprising:
    transmitting light into a clad optical fiber such that the light propagates into a down-tapered or partially unclad segment of the optical fiber and produces evanescent fields at the sample, the sample being located both laterally adjacent and outside the down-tapered or partially unclad segment;
    collecting light emitted into an optical aperture by the sample in response to the step of transmitting light, the optical aperture opening toward a lateral surface of the tapered or partially unclad segment; and
    measuring intensities of said collected light.

12. The method of claim 11, wherein the transmitting sends the light to an untapered segment of the optical fiber, the untapered segment being configured to operate as single-mode optical fiber for the light.

13. The method of claim 12, wherein the optical aperture is oriented to block light emitted by ends of the optical fiber during the step of collecting.

14. The method of claim 12, the collecting is performed in a manner that blocks light received from outside of a solid angle, the solid angle being subtended at the light collection device by the down-tapered or partially unclad segment.

15. The method of claim 12, wherein the step of collecting collects light emitted by the sample into a solid angle of at least π.

16. The method of claim 11, wherein said step of transmitting causes surface plasmons to propagate along said down-tapered or partially unclad segment, the surface plasmons producing at least part of the evanescent fields.

17. An apparatus, comprising:
    a single-mode optical fiber having an optical core and an optical cladding, the fiber having an untapered segment and a tip segment, a portion of the cladding being removed in the tip segment to expose a lateral surface of the optical core; and
    a light collection device having an optical aperture, the aperture being configured to collect light emitted by a sample in response to the sample being located laterally adjacent the exposed lateral surface of the optical core in the tip segment; and
    wherein the optical aperture of the light collection device is configured to block light emitted from ends of the optical fiber.

18. The apparatus of claim 17, further comprising a spectrometer configured to measure light intensities collected by the light collection device and to determine a Raman or luminescence spectrum of the sample from the measured light intensities.

19. The apparatus of claim 17, wherein the tip segment is configured to subject the chemical species on the lateral surface of the optical core in the tip segment to evanescent fields produced by light propagating in the optical fiber.

20. The apparatus of claim 17, wherein the light collection device is configured to block light received from outside of a solid angle, the solid angle being subtended at the light collection device by the down-tapered segment.

* * * * *